US007413816B2

(12) United States Patent
Inoue et al.

(10) Patent No.: US 7,413,816 B2
(45) Date of Patent: Aug. 19, 2008

(54) ORGANIC METALLIC COMPLEX AND ELECTROLUMINESCENT ELEMENT USING THE SAME

(75) Inventors: Hideko Inoue, Kanagawa (JP); Satoshi Seo, Kanagawa (JP); Atsushi Tokuda, Kanagawa (JP); Ryoji Nomura, Kanagawa (JP)

(73) Assignee: Semiconductor Energy Laboratory Co., Ltd., Kanagawa-Ken (JP)

( * ) Notice: Subject to any disclaimer, the term of this patent is extended or adjusted under 35 U.S.C. 154(b) by 11 days.

(21) Appl. No.: 10/736,679

(22) Filed: Dec. 17, 2003

(65) Prior Publication Data
US 2004/0241493 A1 Dec. 2, 2004

(30) Foreign Application Priority Data
Dec. 19, 2002 (JP) .............................. 2002-368990

(51) Int. Cl.
*H01L 51/54* (2006.01)
*C09K 11/06* (2006.01)

(52) U.S. Cl. ..................... 428/690; 428/917; 313/504; 313/506; 257/E51.044; 546/5; 546/6; 546/10; 548/403; 556/137

(58) Field of Classification Search ............... 428/690, 428/917; 313/504, 506; 257/40; 252/301.16; 546/5, 10; 548/403; 556/136, 137
See application file for complete search history.

(56) References Cited

U.S. PATENT DOCUMENTS

| | | | |
|---|---|---|---|
| 5,756,224 | A | 5/1998 | Borner et al. |
| 6,534,434 | B2 | 3/2003 | MacMillan et al. |
| 6,787,249 | B2 | 9/2004 | Seo |
| 6,824,895 | B1 | 11/2004 | Sowinski et al. |
| 6,830,828 | B2 | 12/2004 | Thompson et al. |
| 6,864,628 | B2 | 3/2005 | Yamazaki et al. |
| 6,867,538 | B2 | 3/2005 | Adachi et al. |
| 6,869,697 | B2 * | 3/2005 | Heuer et al. ............... 428/690 |
| 6,894,307 | B2 | 5/2005 | Forrest et al. |
| 6,902,830 | B2 | 6/2005 | Thompson et al. |
| 7,029,766 | B2 | 4/2006 | Huo et al. |
| 7,060,369 | B2 | 6/2006 | Stossel et al. |
| 7,063,900 | B2 | 6/2006 | Shiang et al. |
| 7,078,114 | B2 | 7/2006 | Seo et al. |
| 7,090,930 | B2 | 8/2006 | Robello et al. |
| 7,097,916 | B2 | 8/2006 | Seo et al. |
| 7,098,295 | B2 | 8/2006 | Chen et al. |
| 7,118,812 | B2 | 10/2006 | Deaton et al. |
| 7,147,937 | B2 | 12/2006 | Lussier et al. |
| 7,311,982 | B2 | 12/2007 | Christou et al. |
| 2001/0045565 | A1 | 11/2001 | Yamazaki |
| 2001/0050373 | A1 * | 12/2001 | Yamazaki et al. ............ 257/103 |
| 2002/0034656 | A1 * | 3/2002 | Thompson et al. .......... 428/690 |
| 2003/0059646 | A1 * | 3/2003 | Kamatani et al. ........... 428/690 |
| 2003/0194580 | A1 | 10/2003 | Hamada et al. ............. 428/690 |
| 2004/0072017 | A1 | 4/2004 | Nii et al. |
| 2005/0057151 | A1 | 3/2005 | Kuwabara |

FOREIGN PATENT DOCUMENTS

JP 2002/246172 8/2002

OTHER PUBLICATIONS

Grant & Hackh's Chemical Dictionary 5th ed., 1987, McGraw-Hill, Inc., p. 53.*
CIE Color System [online] [retrieved Aug. 28, 2006] Retrieved from the Internet: <URL: http://hyperphysics.phy-astr.gsu.edu/hbase/vision/cie.html>.*
C.W. Tang et al., "Organic electroluminescent diodes", Applied Physics Letters, vol. 51, No. 12, Sep. 21, 1987, pp. 913-915.
Tetsuo Tsutsui, "The operation mechanism and the light emission efficiency of the organic EL element", Text of the third lecture meeting, Bulletin of Organic Molecular/Bioelectronics Subcommittee, Society of Applied Physics, 1993, pp. 31-37, w/full translation.
D.F. O'Brien et al., "Improved energy transfer in electrophosphorescent devices", Applied Physics Letters, vol. 74, No. 3, Jan. 18, 1999, pp. 442-444.

(Continued)

*Primary Examiner*—Marie R. Yamnitzky
(74) *Attorney, Agent, or Firm*—Nixon Peabody LLP; Jeffrey L. Costellia

(57) ABSTRACT

A white or whitish luminescent material for phosphorescence is provided by synthesizing an organometallic complex that is able to convert a triplet excited state into light emission. In particular, a white electroluminescent device that has a high luminous efficiency and can be manufactured easily is provided by using the organometallic complex to manufacture a white or whitish electroluminescent device. The electroluminescent device is used to provide a light-emitting device with low power consumption. A fluorescent and phosphorescent material represented by a general formula (2) is synthesized. Since this material can emit both components of fluorescence and phosphorescence in the region of visible light, white or whitish luminescence can be achieved, which is applied to an electroluminescent device or a light-emitting device

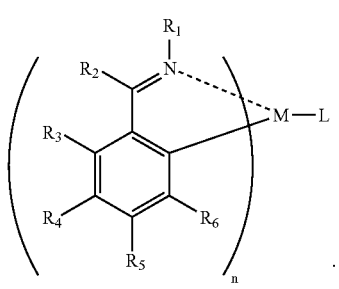

(Formula 2)

43 Claims, 5 Drawing Sheets

OTHER PUBLICATIONS

Tetsuo Tsutsui et al., "High Quantum Efficiency in Organic Light-Emitting Devices with Iridium-Complex as a Triplet Emissive Center", Japanese Journal of Applied Physics, vol. 38, Dec. 15, 1999, pp. L1502-L1504.

Brian W. D'Andrade et al., "White Light Emission Using Triplet Excimers in Electrophosphorescent Organic Light-Emitting Devices", Advanced Materials, 14, No. 15, Aug. 5, 2002, pp. 1032-1036.

Buey et al., "*Platinum Orthometalated Liquid Crystals Compared With Their Palladium Analogues. First Optical Storage Effect in an Organometallic Liquid Crystal*", Chemistry of Materials, 1996, vol. 8, No. 9, pp. 2375-2381, Sep. 1, 1996.

Diez et al., "*Ferroelectric Liquid Crystal Behavior in Platinum Orthometallated Complexes*", Journal of Materials Chemistry, 2002, vol. 12, No. 12, pp. 3694-3698, Dec. 1, 2002.

Cave et al., "*Cyclopalladated Schiff's Base Liquid Crystals: The Effect of the ACAC Group on the Thermal Behaviour*" Journal of Organometallic Chemistry, 1998, vol. 555, pp. 81-88.

Saccomando et al., "*Chiral Cyclopalladated Liquid Crystals From Amino Acids*", Journal of Organometallic Chemistry, 2000, vol. 601, pp. 305-310.

International Search Report (Application No. PCT/JP03/15765) Dated: Apr. 6, 2004 (in Japanese).

* cited by examiner

ORGANIC METALLIC COMPLEX AND ELECTROLUMINESCENT ELEMENT USING THE SAME

TECHNICAL FIELD

The present invention relates to a compound that is able to convert a triplet excited state into light emission. The present invention also relates to an electroluminescent device that has an anode, a cathode, and a layer including an organic compound (hereinafter, referred to as "electroluminescent layer") from which light emission is obtained by applying electric field, where the electroluminescent layer includes a compound that is able to convert a triplet excited state into light emission, and a light-emitting device using the electroluminescent device.

BACKGROUND ART

When light is absorbed by an organic compound (organic molecule), the organic compound (organic molecule) gets to have energy (an excited state). Through this excited state, various photochemical reactions may be developed or light emission (luminescence) may be generated, and various applications have been tried. In particular, as an application field of a light-emitting compound, an electroluminescent device (a device that emits light by applying electric field) can be given.

In the case of using an organic compound as a light emitter, the emission mechanism of an electroluminescent device is a carrier injection type. In other words, by applying a voltage with an electroluminescent layer sandwiched between electrodes, an electron injected from a cathode and a hole injected from an anode are recombined in the electroluminescent layer to form a molecule in an excited state (hereinafter, referred to as an exited molecule), and energy is released to emit light while the excited molecule moves back toward the ground state.

In the foregoing electroluminescent device, the electroluminescent layer is generally formed of a thin film about below 1 µm. Further, since the foregoing electroluminescent device is a self-luminous device, where the electroluminescent layer itself emits light, a backlight that is used for a conventional liquid crystal display is unnecessary. Therefore, a great advantage of using such devices is that it is possible to manufacture a significantly thin and a lightweight display.

In the case of an electroluminescent layer with a thickness approximately from 100 to 200 nm, for example, the time from an injection of carriers to their recombination is about several ten nanoseconds considering the carrier mobility of the electroluminescent layer. Even when processes from the recombination of the carriers to light emission are included, only time on the microsecond time scale is required to reach light emission. Thus, the fairly high response speed is also one of the features.

In addition, since the foregoing electroluminescent device is a carrier injection type light-emitting device, driving by DC voltage is possible, and it is unlikely that a noise is generated. As for the driving voltage, an uniform ultra thin film with a thickness of approximately 100 nm is first used as the electroluminescent layer, a material for an electrode is also selected to reduce a carrier injection barrier against the electroluminescent layer, and a heterostructure (two-layer structure) is additionally introduced. Accordingly, a sufficient luminance of 100 cd/m$^2$ can be obtained at 5.5V (refer to Non-Patent Document 1, for example).

(Non-Patent Document 1)

C. W. Tang and S. A. Vanslyke, "Organic electroluminescent diodes", Applied Physics Letters, vol. 51, No. 12, 913-915 (1987)

The electroluminescent device has been attracting attention as a next-generation flat panel display in terms of the features such as the thin thickness and the lightweight, the high speed response, and the low DC voltage drive. In addition, relatively favorable visibility can be obtained since the electroluminescent device is a self-luminous device that has a wide viewing angle, and the electroluminescent device is considered to be effective as the device for a display screen of a portable device.

By the way, light emission observed in the foregoing electroluminescent device is a luminous phenomenon in an excited molecule moving back toward a ground state. When excited, the molecule formed from an organic molecule can take two kinds of state: a singlet excited state (S*) and a triplet excited state (T*). In addition, the statistic generation ratio in an electroluminescent device is considered to be S*:T*=1:3 (see Non-Patent Document 2, for example).

(Non-Patent Document 2)

Tetsuo TSUTSUI, Text of the third lecture meeting, Bulletin of Organic Molecular/Bioelectronics Subconirmittee, Society of Applied Physics, p. 31-37 (1993)

However, in the case of a general organic compound, luminescence from the triplet exited state (phosphorescence) is not observed at room temperature while only luminescence from the singlet exited state (fluorescence) is observed generally. This is because T* (S$_0$ transition (phosphorescence process)) becomes a forbidden transition and S* (S$_0$ transition (fluorescence process)) becomes an allowed transition since an organic compound generally has a ground state of a singlet state (S$_0$). In other words, only the singlet excited state contributes to luminescence generally.

Consequently, the internal quantum efficiency (the ration of photons generated to injected carriers) in an electroluminescent device is assumed to have a theoretical limit of 25% in accordance with S*:T*=1:3.

Further, generated light is not all coupled out to the outside, and it is not possible to take a portion of the light out due to inherent refractive indexes of a constituent material of an electroluminescent device and a material of a substrate. The ratio of light taken out to the outside to generated light is referred at as a light-extraction efficiency, it is said that the light-extraction efficiency is only about 20% in an electroluminescent device that has a glass substrate.

Consequently, it is said that the ratio of photons that can be taken out finally to the outside to the number of the injected carriers (hereinafter, "external quantum efficiency") has a theoretical limit of 25%×20%=5% if injected carriers are all formed into excited molecules. In other words, if all of the carriers are recombined, it is conceivable that only 5% thereof can be taken out as light.

However, in these years, an electroluminescent device that is able to convert an energy released in moving back toward a ground state from a triplet excited state (T*) (hereinafter, referred to as "triplet excitation energy") into light emission has been made in public one after the other, and a high luminous efficiency thereof has been attracting attention (refer to Non-Patent Document 3 and Non-Patent Document 4, for example).

(Non-Patent Document 3)

D. F. O'Brien, M. A. Baldo, M. E. Thompson and S. R. Forrest, "Improved energy transfer in slctrophosphorescent devices", Applied Physics Letters, vol. 74, No. 3, 442-444 (1999)

(Non-Patent Document 4)

Tetsuo TSUTSUI, Moon-Jae YANG, Masayuki YAHIRO, Kenji NAKAMURA, Teruichi WATANABE, Taishi TSUJI, Yoshinori FUKUDA, Takeo WAKIMOTO and Satoshi MIYAGUCHI, "High Quantum Efficiency in Organic Light-Emitting Devices with Iridium-Complex as a Triplet Emissive center", Japanese Journal of Applied Physics Vol. 38, pp. L1502-L1504 (1999)

A porphyrin complex that has platinum as a central metal and an organometallic complex that has iridium as a central metal are respectively used in Non-Patent Document 3 and in Non-Patent Document 4, and both of the complexes are of a phosphorescent material that has a third-series transition element introduced as a central metal, which includes one that well exceeds the foregoing theoretical limit 5% of the external quantum efficiency. In other words, an electroluminescent device using a phosphorescent material can achieve a higher external efficiency than conventional one. Then, as the external efficiency is higher, the luminance is improved.

Therefore, an electroluminescent device using a phosphorescent material is considered to occupy an important position in a future development as a means for accomplishing luminescence with a high luminance and a high luminance efficiency.

As described above, a phosphorescent material is useful for being applied to electroluminescent devices, which is expected. However, it is still the case that the number thereof is small. The iridium complex that is used in Non-Paten Document 4 is one of organometallic complexes referred to as an orthometalated complex. Since this complex has a phosphorescence lifetime of several hundreds nanoseconds and a high phosphorescence quantum yield, the decrease in efficiency associated with an increase in luminance is small as compared to the porphyrin complex. From that viewpoint, the foregoing organometallic complex using the heavy metal is one of guidelines for synthesizing a phosphorescent material.

By the way, an electroluminescent device has been actively developed for being applied to displays. Above all, the development of a device that can emit white light has been distinctly attracting attention. This is because full color display is possible when a color filter is attached to a display device, in addition to applications as mono-color display and lighting such as a backlight.

Since a light-emitting device with a filter passed through has an usability of light lowered, a device that can achieve high-luminance while light emission with lower power consumption is strongly required. In addition, considering the application as lighting, it is no mistake that a higher luminance is required. Therefore, it can be said that the use of an electroluminescent device using a phosphorescent material for realizing white light emission is the most effective means.

In the case of a conventional electroluminescent device using a phosphorescent material for white light emission, a method such as a method of mixing materials that respectively emit R (red), G (green), and B (blue) to form a thin film, a method of laminating layers that respectively emit R (red), G (green), and B (blue), or a method of combining complementary colors (a blue-green color and an orange color, for example) (refer to Non-Patent Document 5, for example) is considered. However, since a plurality of luminescent materials that have different emission wavelengths are needed in any case in order to obtain a spectrum of white light, there is a problem that a driving voltage is increased. In addition, since it is necessary to combine a hole blocking layer in order to obtain a high luminous efficiency from an electroluminescent device using a phosphorescent material, a quite complicated device structure is required.

(Non-Patent Document 5)

Brian W. D'Andrade, Jason Brooks, Vadim Adamovich, Mark E. Thompson, and Stephen R. Forrest, "White Light Emission Using Triplet Excimers in Electrophosphorescent Organic Light-Emitting Device", Advanced Materials, 14, No. 15, 1032-1036 (2002)

As above, since a planar source for white light emission_is composed of a plurality of materials combined quite intricately, a manufacturing process is not only controlled with difficulty but also is made cumbersome and complicated.

DISCLOSURE OF INVENTION (Problem to be Solved by the Invention)

It is an object of the present invention to provide a novel white or whitish luminescent material by synthesizing an organometallic complex that is able to convert a triplet excited state into luminescence.

In addition, it is particularly an object of the present invention to provide a white electroluminescent device that has a high luminous efficiency and can be easily manufactured by using the organometallic complex to manufacture a white or whitish electroluminescent device that has a simple device structure.

Further, it is an object of the present invention to provide a light-emitting device with low power consumption by using the electroluminescent device to manufacture a light-emitting device. The light-emitting device in the specification indicates a light-emitting device and an image display device that use an electroluminescent device. In addition, a module that has a connecter such as an anisotropic conductive film (EPC: Flexible Printed Circuit) or TAB (Tape Automated Bonding) attached to an electroluminescent device, a module that has a TAB tape or a TCP (Tape Carrier Package) attached, a module that has a printed wiring board provided at the tip of a TAB tape or a TCP, and a module that has an electroluminescent device directly mounted with an IC (integrated circuit) by a COG (Chip On Glass) method are all included in the light-emitting device.

(Means for Solving the Problem)

The inventors have focused on an organometallic compound that has an element of Group 9 or an element of Group 10 as a center, which can be formed in the case of using a ligand shown by the following general formula 1.

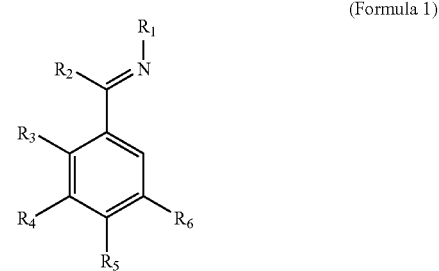

(Formula 1)

Then, the inventors have found that a complex represented by the following general formula 2, which is synthesized by orthometallation of the ligand of the general formula 1, has both components of fluorescence and phosphorescence of in the region of visible light. Since emission wavelengths of fluorescence and phosphorescence of this complex are observed respectively in the side of shorter wavelengths and in the side of longer wavelengths, it is a feature to be a white or whitish lighting color.

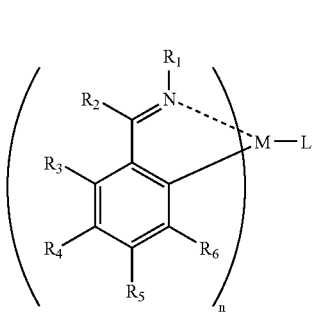

(Formula 2)

(where $R_1$ is an alkyl group, an aryl group, a substituted aryl group, a heterocyclic group or a substituted heterocyclic group; $R_2$ is hydrogen, an alkyl group, an aryl group, a substituted aryl group, a heterocyclic group, or a substituted heterocyclic group; $R_3$, $R_4$, $R_5$, and $R_6$ may be identical or different, and are individually hydrogen, halogen, an alkyl group, an alkoxyl group, an aryl group, a substituted aryl group, a heterocyclic group, or a substituted heterocyclic group; M is an element of Group 9 or an element of Group 10, and n=2 when the M is the element of Group 9 or n=1 when the M is the element of Group 10; and L is a monoanionic ligand having a β-diketone structure, a monoanionic bidentate ligand having a carboxyl group, or a mono anionic bidentate ligand having a phenolic hydroxyl group.

Consequently, it is an aspect of the present invention to provide the organometallic complex represented by the aforementioned general formula 2.

For more efficient phosphorescence, a heavy metal is preferred as the central metal in terms of heavy atom effect. Therefore, one feature of the present invention is that the central metal M is iridium or platinum in the aforementioned general formula.

In addition, any of monoanionic ligands shown by structure formulas 3 to 9 below is preferable although the ligand L is any of a monoanionic ligand having a β-diketone structure, a monoanionic bidentate ligand having a carboxyl group, and a monoanionic bidentate ligand having a phenolic hydroxyl group.

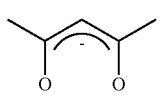

(Formula 3)

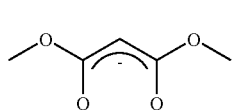

(Formula 4)

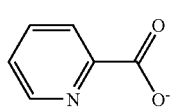

(Formula 5)

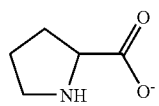

(Formula 6)

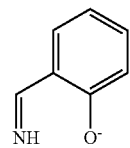

(Formula 7)

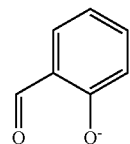

(Formula 8)

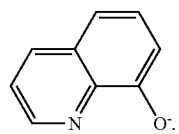

(Formula 9)

By the way, since the organometallic complex according to the present invention can convert triplet excitation energy into light emission, an efficient device with white or whitish luminescence becomes possible by applying the organometallic complex to an electroluminescent device, which is quite efficient. Consequently, the present invention also includes an electroluminescent device that uses the organometallic complex according to the present invention.

Since the thus obtained electroluminescent device according to the present invention can realize a high luminous efficiency, a light-emitting device that uses this as a light-emitting element (an image display device or a light-emitting device) can realize low power consumption. Consequently, the present invention also includes a light-emitting device that uses the organometallic complex according to the present invention.

EFFECT OF THE INVENTION

A novel organometallic compound can be provided by carrying out the present invention. In addition, an electroluminescent device that has a high luminous efficiency can be provided by using the organometallic compound to manufacture an electroluminescent device. Further, a light-emitting device and an electronic device with low power consumption can be provided by using the organometallic complex to manufacture a light-emitting device and an electronic device.

BEST MODE FOR CARRYING OUT THE INVENTION

The ligand represented by the aforementioned general formula 1 can be synthesized in accordance with the following synthesis scheme 10.

(Formula 10)

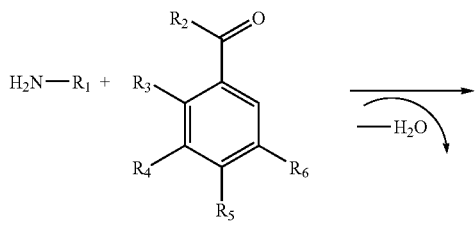

-continued

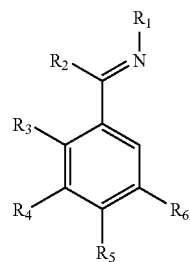

Thus obtained ligand of the general formula 1 is used to form the organometallic complex according to the present invention (general formula 2). As the orthometallation reaction at this moment, a known synthesis method may be used.

In synthesizing an organometallic complex with iridium as a central metal according to the present invention, for example, iridium chloride hydrate is used as a raw material to synthesize a chlorine-bridged dinuclear complex first by mixing the iridium chloride hydrate with the ligand of the general formula 1 and refluxing in a nitrogen atmosphere (the following synthesis scheme 11). Next, the chlorine bridge is cut with the ligand L to obtain the organometallic complex according to the present invention by mixing the obtained dinuclear complex and a raw material for the ligand L and refluxing in a nitrogen atmosphere (the following synthesis scheme 12).

(Formula 11)

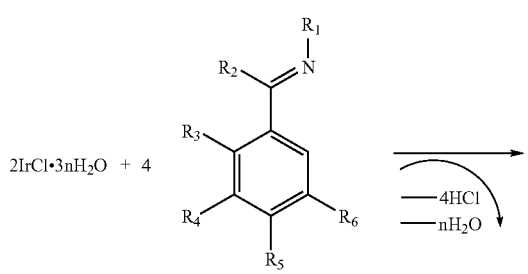

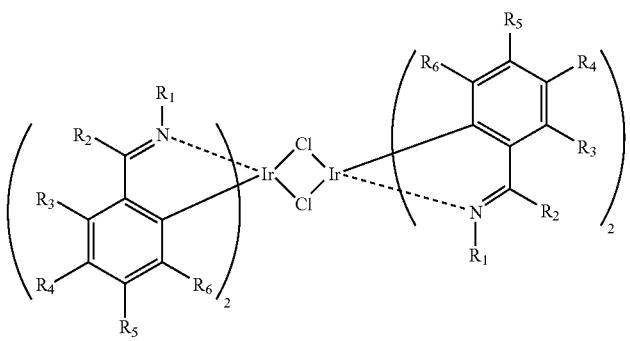

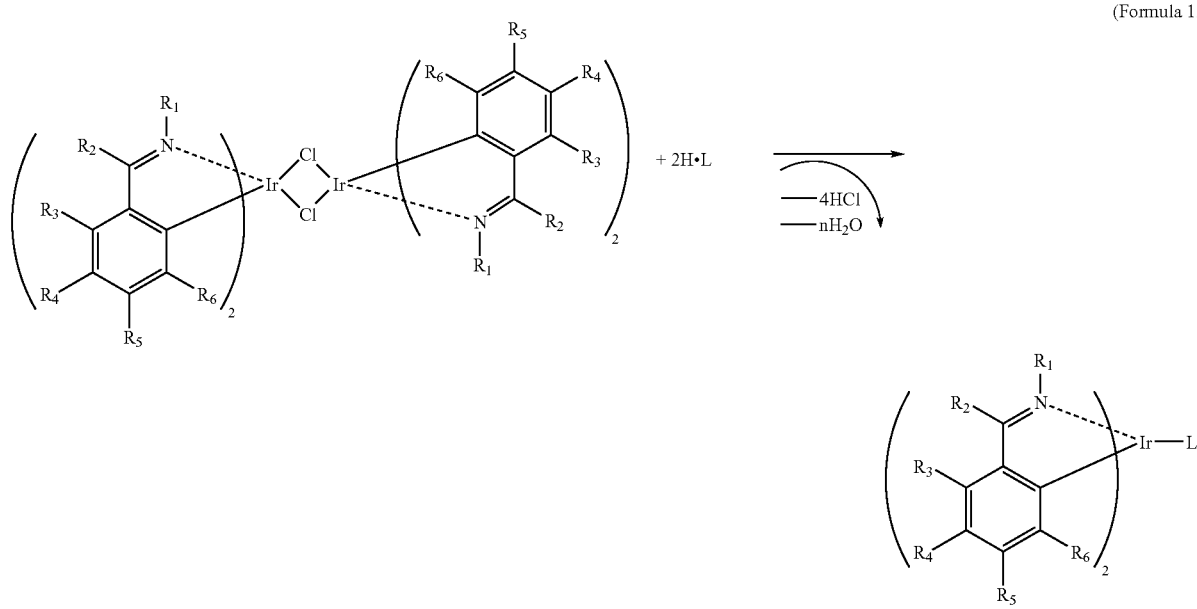

The synthesis method of the organometallic complex, which is used in the present invention, is not limited to the synthesis method shown above.

In addition, while the organometallic complex according to the present invention can be used as a fluorescent and phosphorescent material, it is believed that it is more preferable that the substituent $R_2$ in the aforementioned general formula 2 is not hydrogen but an electron donating group such as an alkyl group in order to efficiently realize the both components of fluorescence and phosphorescence.

Next, a mode where the fluorescent and phosphorescent material according to the present invention is applied to an electroluminescent device will be described below.

Embodiment Mode 1

In Embodiment Mode 1, a device structure of an electroluminescent device that has a light-emitting layer including an organometallic complex according to the present invention, a hole injection layer comprising a low molecular weight material, a hole transport layer, a hole blocking layer, and an electron transport layer will be described with reference to FIG. 1.

Figure 1:
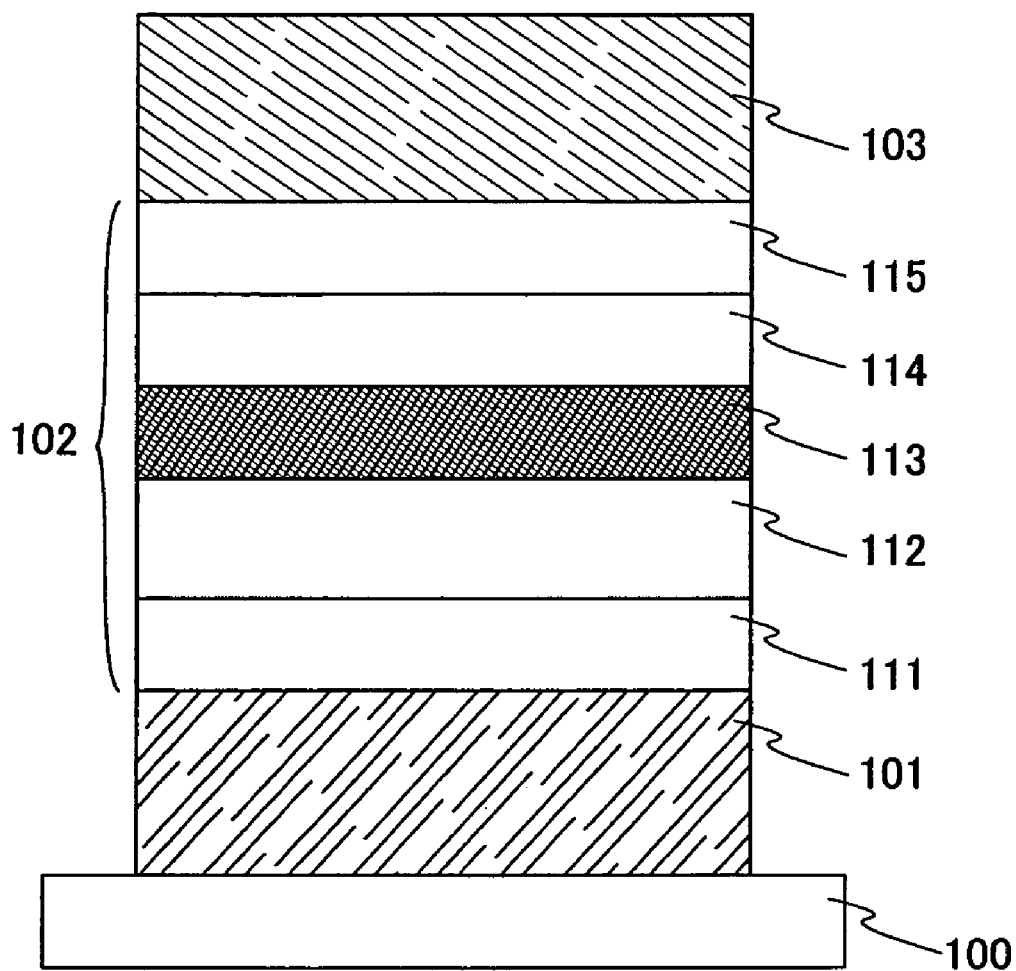
FIG. 1 is a diagram describing a device structure of an electroluminescent device in Embodiment Mode 1.

FIG. 1 has a structure where a first electrode 101 is formed on a substrate 100, an electroluminescent layer 102 is formed on the first electrode 101, and a second electrode 103 is formed thereon.

Here, as a material that is used for the substrate 100, a material that is used in a conventional electroluminescent device may be used, and a substrate comprising such as glass, quartz, or transparent plastic can be used.

Besides, the first electrode 101 in Embodiment Mode 1 functions as an anode and the second electrode 103 functions as a cathode.

In other words, the first electrode 101 is formed of an anode material, and it is preferable to use a metal, an alloy, an electrically conductive compound, and a mixture of these, which have a large work function (a work function of 4.0 eV or more), as the anode material that can be used here. As a specific example of the anode material, gold (Au), platinum (Pt), nickel (Ni), tungsten (W), chromium (Cr), molybdenum (Mo), iron (Fe), cobalt (Co), copper (Cu), palladium (Pd), a nitride of a metal material (TiN), or the like can be used in addition to ITO (indium tin oxide) and IZO (indium zinc oxide) of indium oxide mixed with zinc oxide (ZnO) at 2 to 20[%].

On the other hand, it is preferable to use a metal, an alloy, an electrically conductive compound, and a mixture of these, which have a small work function (a work function of 3.8 eV or less), as a cathode material that is used for forming the second electrode 103. As a specific example of the cathode material, a rare-earth metal can be used for the formation in addition to an element belonging to Group 1 or Group 2 of the periodic table of the element, that is, an alkali metal such as Li or Cs, and an alkali earth element such as Mg, Ca, or Sr, and an alloy (Mg:Ag, Al:Li) and a compound (LiF, CsF, CaF$_2$) including these, and it is also possible to further laminate a metal (including an alloy) such as Al, Ag, or ITO for the formation.

In addition, a thin film of the foregoing anode material and a thin film of the cathode material are formed by evaporation, sputtering, or the like to respectively form the first electrode 101 and the second electrode 103, which preferably have a film thickness of 10 to 500 nm.

Besides, in the electroluminescent device according to the present invention, light generated by recombination of carriers in the electroluminescent layer is emitted from one or both of the first electrode 101 and the second electrode 103 to the outside. In other words, the first electrode 101 is formed of a translucent material in the case where light is emitted from the side of the first electrode 101 while the second electrode 103 is formed of a translucent material in the case where light is emitted from the side of the second electrode 103.

In addition, the electroluminescent layer 102 uses a single layer, or is formed by laminating a plurality of layer. In Embodiment Mode 1, the electroluminescent layer 102 is formed by laminating a hole injection layer 111, a hole transport layer 112, a light-emitting layer 113, a hole blocking layer 114, and an electron transport layer 115.

As a hole injection material for forming the hole injection layer 111, a phthalocyanine-based compound is efficient. For example, phthalocyanine (abbreviation: referred to as $H_2$—Pc), copper phthalocyanine (abbreviation: referred to as Cu—Pc), and the like can be used.

As a hole transport material for forming the hole transport layer 112, an aromatic amine-based (that is, one that has a bond of benzene ring-nitrogen) compound is widely used. As materials that are used widely, for example, in addition to 4,4'-bis [N-(3-methylphenyl)-N-phenyl-amino]-biphenyl (abbreviation: TPD), a derivative thereof such as 4,4'-bis[N-(1-naphthyl)-N-phenyl-amino]-biphenyl (abbreviation: α-NPD) and star burst aromatic amine compounds such as 4,4',4"-tris (N,N-diphenyl-amino)-triphenylamine (abbreviation: TDATA) and 4,4',4"-tris[N-(3-methylphenyl)-N-phenyl-amino]-triphenylamine (abbreviation: MTDATA) can be given.

The light-emitting layer 113 includes the organometallic complex previously shown by the general formula 2, and is formed by co-evaporation of this organometallic complex and a host material. As the host material, a known material can be used, and 4,4'-bis(N-carbazolyl)-biphenyl (abbreviation: CBP), 2,2'2"-(1,3,5-benzenetriyl)-tris[1-phenyl-1Hbenzimidazole] (abbreviation: TPBI), and the like can be given.

As a hole blocking material for forming the hole blocking layer 114, bis(2-methyl-8-quinolinolate)-(4-phenylphenolato)-aluminum (abbreviation: BAlq), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation; BCP), or the like can be used.

As an electron transport material in the case of forming the electron transport layer 115, a metal complex that has a quinoline skeleton or a benzoquinoline skeleton such as tris (8-quinolinolato) aluminum (abbreviation: $Alq_3$), tris (5-methyl-8-quinolinolato) aluminum (abbreviation: $Almq_3$), or bis (10-hydroxybenzo[h]-quinolinato) beryllium (abbreviation: $BeBq_2$), and BAlq mentioned above are preferred. In addition, a metal complex that has an oxazole-based ligand or a thiazole-based ligand such as bis [2-(2-hydroxyphenyl)-benzothiazolato]zinc (abbreviation: $Zn(BTZ)_2$) can also be used. In addition to the metal complexes, 2-(4-biphenyl)-5-(4-tert-butylphenyl)-1,3,4-oxadiazole (abbreviation: PBD), the aforementioned OXD-7, TAZ, p-EtTAZ, Bphen, and BCP, and the like can be used as the electron transport material.

In this way, it is possible to form an electroluminescent device that has the light-emitting layer 113 including the organometallic complex according to the present invention, the hole injection layer 111 comprising the low molecular weight, the hole transport layer 112, the hole blocking layer (hole blocking layer) 114, and the hole transport layer 115.

In Embodiment Mode 1, the organometallic complex according to the present invention is used as a guest material in the light-emitting layer 113, the electroluminescent device is the device that has luminescence obtained from the organometallic complex according to the present invention as a lighting color.

Embodiment Mode 2

Figure 2:
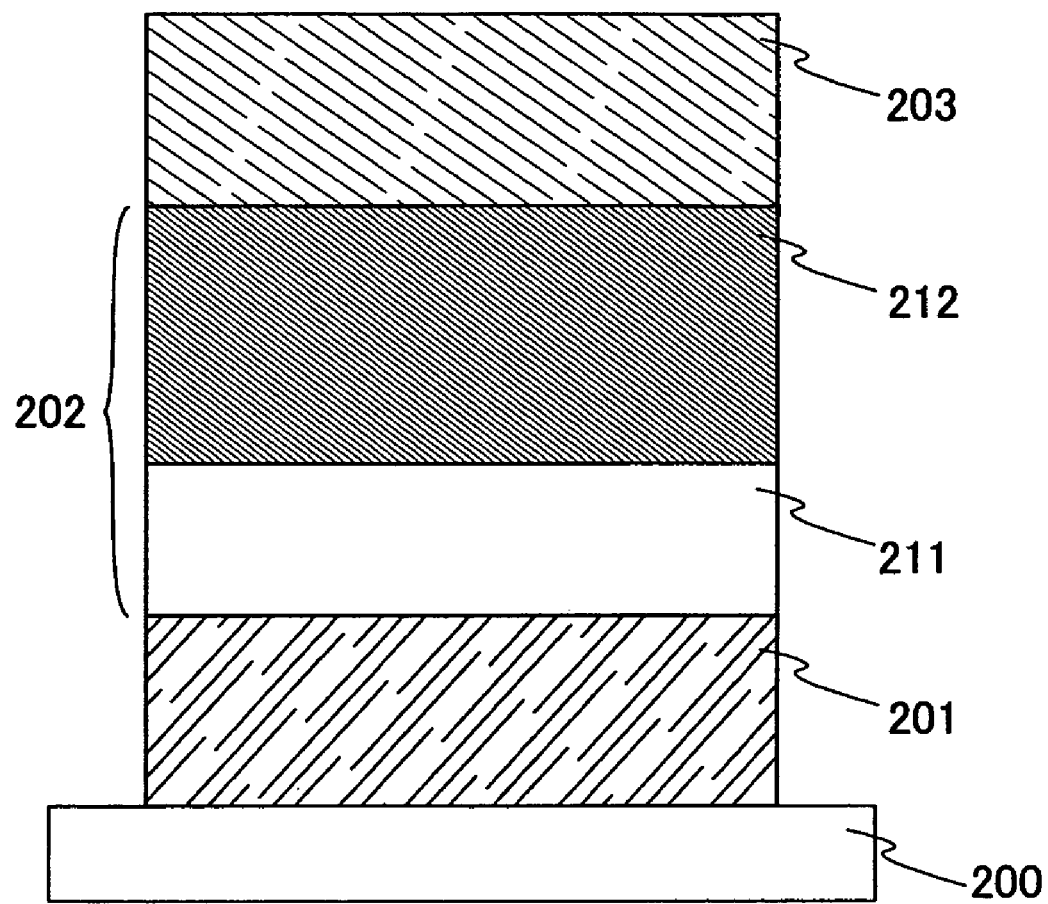
FIG. 2 is a diagram describing a device structure of an electroluminescent device in Embodiment Mode 2.

In Embodiment Mode 2, a device structure of an electroluminescent device that has a light-emitting layer including an organometallic complex according to the present invention and a hole injection layer comprising a polymer material, which are formed with a wet process, will be described with reference to FIG. 2.

Since it is possible to use the same materials as those in Embodiment Mode 1 to form a substrate 200, a first electrode 201, and a second electrode 203 in the same way, descriptions thereof are omitted.

In addition, an electroluminescent layer 202 is formed by laminating a plurality of layers, in Embodiment Mode 2, formed by laminating a hole injection layer 211 and a light-emitting layer 212.

As a hole injection material for the hole injection layer, polythiophene dioxythiophene (abbreviation: PEDOT) doped with polystyrene sulfonate (abbreviation: IS PSS), polyaniline, polyvinyl carbazole (abbreviation: PVK), and the like can be used.

The light-emitting layer 212 includes the organometallic complex according to the present invention, which is previously shown by the general formula 2, as a guest compound. As a host material, a bipolar material may be used, or a hole transport material and an electron transport material may be mixed alternatively to be bipolar. Here, a hole transport polymer compound (PVK, for example) and the aforementioned electron transport material (PBD, for example) are dissolved in the same solvent at 7:3 (molar ratio) first, and an appropriate amount of the organometallic complex according to the present invention (approximately 5 wt %) is further added to prepare a solution. The light-emitting layer 212 can be obtained by wet application of this solution and baking.

In this way, it is possible to obtain an electroluminescent device that has the light-emitting layer 212 including the organometallic complex according to the present invention and the hole injection layer 211 comprising the polymer material, which are formed with a wet process.

In Embodiment Mode 2, the organometallic complex according to the present invention is used as a guest material in the light-emitting layer 212, the electroluminescent device is a light-emitting device that has luminescence obtained from the organometallic complex according to the present invention as a lighting color.

Embodiments

SYNTHESIS EXAMPLE

The present synthesis example will exemplify a synthesis method of an organometallic complex according to the present invention, represented by the following structure formula 13.

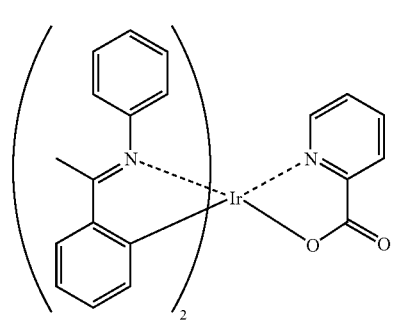

(Formula 13)

First, after refluxing an equimolar amount of acetophenone and anyline in ethanol for 48 hours, a ligand represented by the following structure formula 14 was obtained by removing the solvent (umber and oily).

(Formula 14)

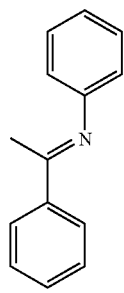

Next, iridium chloride ($IrCl_3.HCl.H_2O$) and 2.5 equivalents of the structure formula 14 were refluxed in a mixed solvent of 2-ethoxyethanol and water at 3:1 in a nitrogen atmosphere for 16 hours to obtain a dinuclear complex of the flowing structure formula 15. The obtained powder was filtered, and subjected to air drying after washing with ethanol and acetone.

(Formula 15)

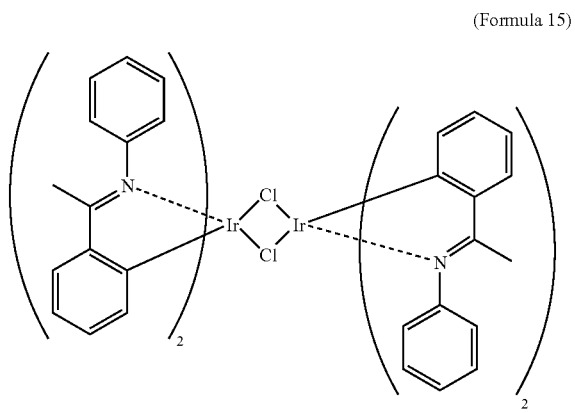

Further, the structure formula, 3 equivalents of picolinic acid, and 10 equivalents of sodium carbonate were refluxed in 2-ethoxyethanol in a nitrogen atmosphere for 16 hours. After removing the solvent, the product was purified by a column chromatography, and recrystallized to obtain the compound of the aforementioned structure formula 13, which is the object.

Figure 3:
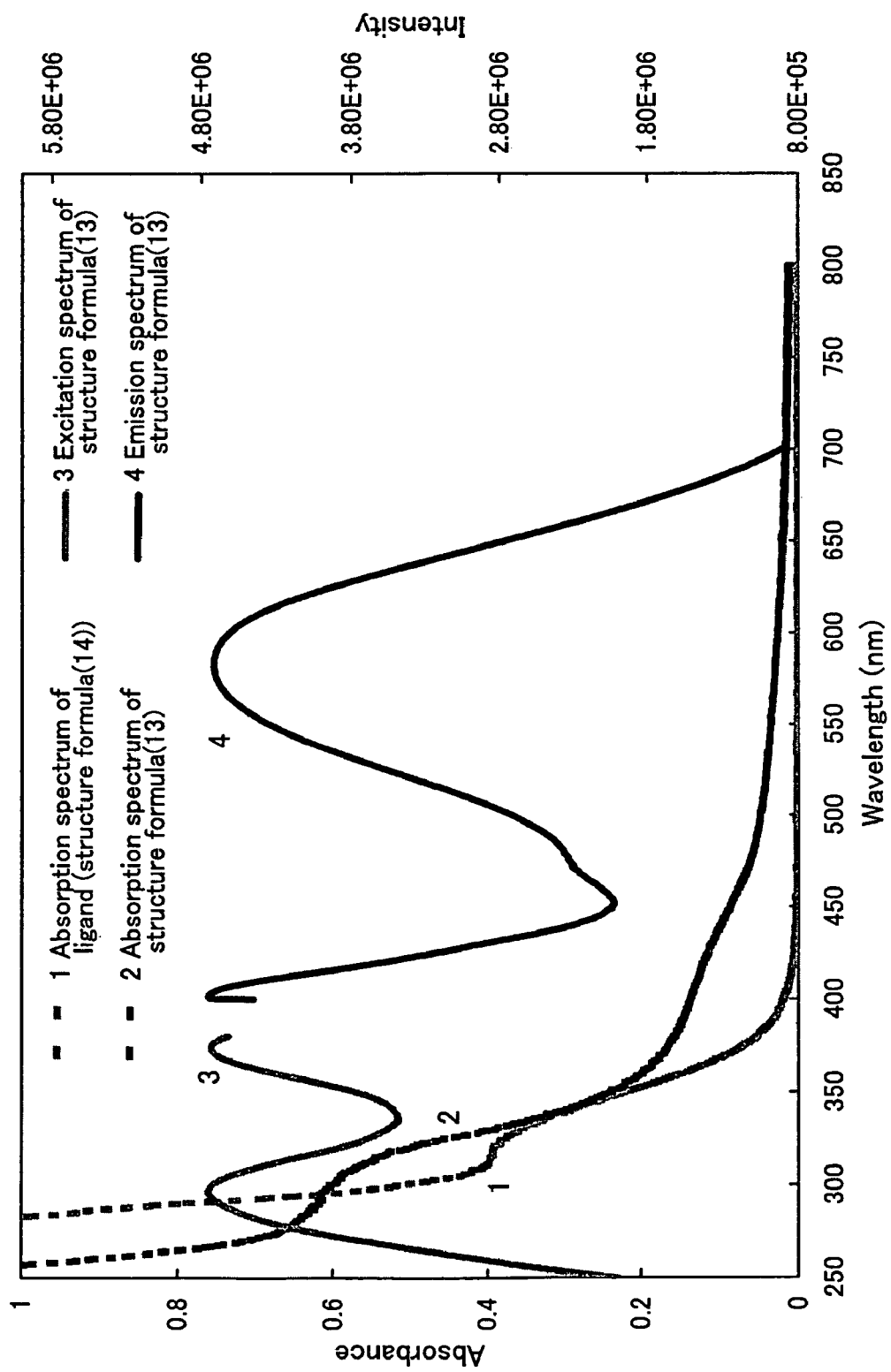
FIG. 3 is a graph showing absorption, excitation, and emission spectra of an organometallic complex according to the present invention.

FIG. 3 shows an absorption spectrum, an excitation spectrum, and an emission spectrum (PL) of the obtained organometallic complex according to the present invention (structure formula 13). In FIG. 3, an absorption spectrum of the ligand (structure formula 14) is also shown together.

As shown in FIG. 3, an absorption spectrum 2 has absorption in the side of longer wavelengths (around 420 nm and 500 to 600 nm) as compared to a spectrum 1 of the ligand, and the broad absorption at 500 to 600 nm particularly suggests triplet MLCT (Metal to Ligand Charge Transfer). In addition, an excitation spectrum 3 has two peaks observed, and an emission spectrum 4 is bluish white luminescence with peaks at about 402 nm and 585 nm. It is believed that the luminescence in the side of shorter wavelengths is a luminescent due to a fluorescent process and the luminescence in the side of longer wavelengths is a luminescence due to a phosphorescent process.

Embodiment 1

Figure 4:
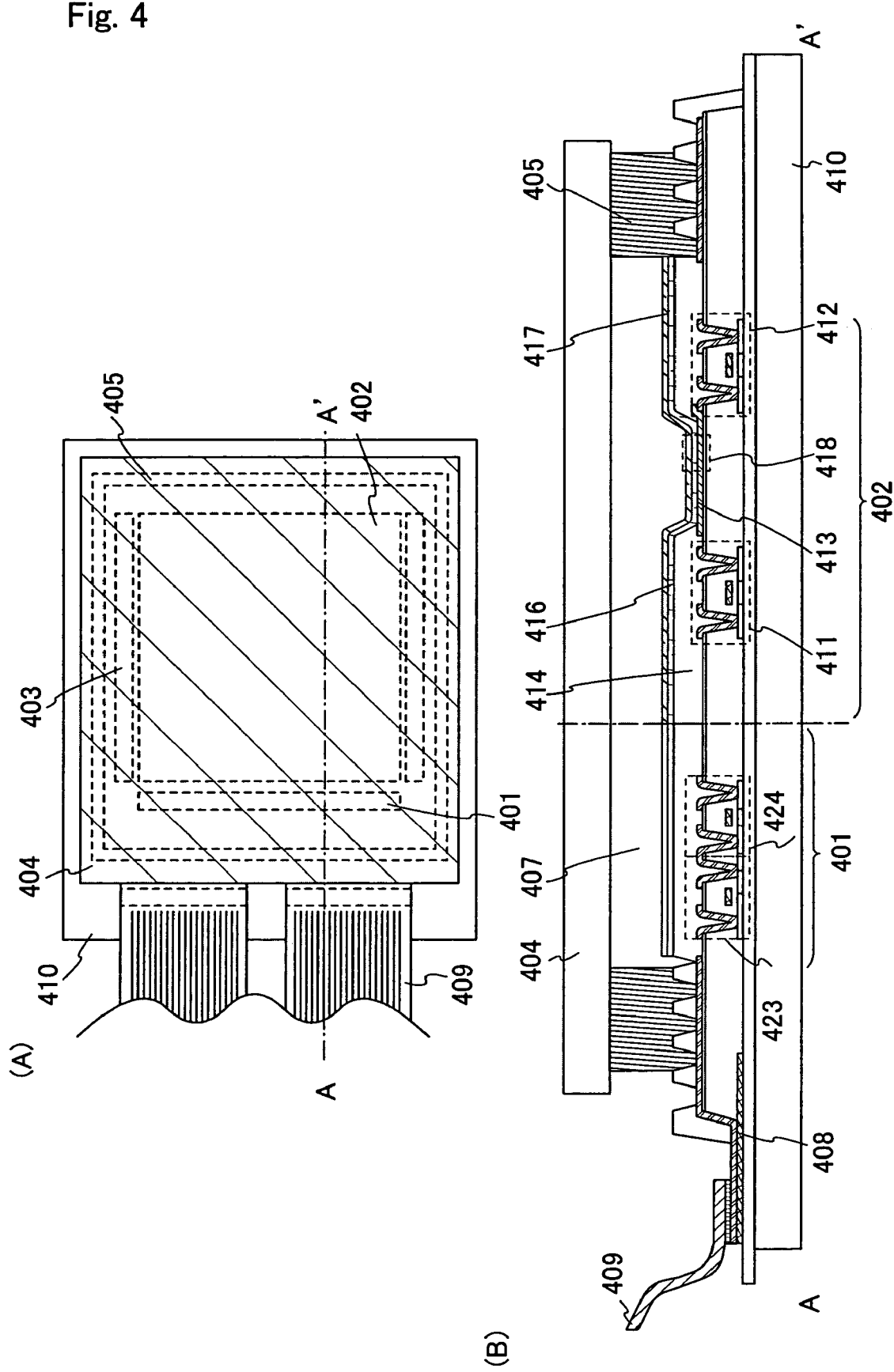
FIGS. 4(A) and 4(B) are diagrams describing a light-emitting device according to the present invention.

In the present embodiment, a light-emitting device that has an electroluminescent device according to the present invention in a pixel portion will be described with reference to FIG. 4(A) and FIG. 4(B). FIG. 4(A) is a top view showing the light-emitting device and FIG. 4(B) is a sectional view of FIG. 4(A) cut along A-A'. Reference numeral 401 indicated by a dotted line denotes a driver circuit portion (a source side driver circuit), 402 is a pixel portion, and 403 is a driver circuit portion (a gate side driver circuit). In addition, reference numeral 404 denotes a sealing substrate and 405 denotes a sealing agent. The inside 407 surrounded by the sealing agent 405 is space.

Reference numeral 408 denotes a wiring for transmitting signals to be input to the source side driver circuit 401 and the gate side driver circuit 403, and receives a video signal, a clock signal, a start signal, a reset signal, and the like from FPC (Flexible Printed Circuit) 409 that serves as an external input terminal. Though only the FPC is shown in the figure here, a printed wiring board (PWB) may be attached to the FPC. A light-emitting device in the specification includes not only a light-emitting device body but also a state where an FPC or a PWB is attached thereto.

Next, the sectional structure will be explained with reference to FIG. 4(B). The driver circuits and the pixel portion are formed over a device substrate 410. Here, the source side driver circuit 401 as the driver circuit portion and the pixel portion 402 are shown.

In the source side driver circuit 401, a CMOS circuit is formed of a combination of an n-channel TFT and a p-channel TFT. The TFTs forming the driver circuit may also be formed of a known CMOS circuit, PMOS circuit, or NMOS circuit. Although the present embodiment shows a driver integrated type in which a driver circuit is formed over a device substrate, which is not always necessary, the driver circuit can be formed not over the device substrate but at the outside thereof.

The pixel portion 402 is formed of a plurality of pixels, each including a switching TFT 411, a current controlling TFT 412, and a first electrode 413 connected to a drain thereof electrically. In addition, an insulator 414 is formed to cover an edge of the first electrode 413. Here, a positive photosensitive acrylic resin film is used to form the insulator 414.

Besides, in order to obtain a favorable coverage, a curved surface with a curvature is formed on a top portion or bottom potion of the insulator 414. For example, in the case of using positive photosensitive acrylic as a material of the insulator 414, it is preferable that only the top portion of the insulator 414 has a curved surface with a curvature radius (0.2 μm to 3 μm). In addition, any of a photosensitive negative type that becomes insoluble in an etchant by light and a positive type that becomes soluble in an etchant by light can be used as the insulator 414.

On the first electrode 413, an electroluminescent layer 416 and a second electrode 417 are respectively formed. Here, as a material that is used for the first electrode 413 functioning as an anode, it is preferable to use a material that has a large work function. For example, in addition to single layers such as an ITO (indium tin oxide) film, an indium zinc oxide (IZO) film, a titanium nitride film, a chromium film, a tungsten film, a Zn film, and a Pt film, a laminate of a titanium nitride film and a film including aluminum as its main component, a three-layer structure of a titanium nitride film, a film including aluminum as its main component, and a titanium nitride film, and the like can be used. When a laminated structure is employed, the resistance as a wiring is low, favorable ohmic contact can be taken, and it is possible to function as an anode.

The electroluminescent layer 416 is formed by evaporation that uses an evaporation mask or by inkjet. For the electroluminescent layer 416, as a part thereof, the organometallic complex (the foregoing general formula 2) according to the present invention is used, and as the other materials that can be used in combination, a low molecular weight material and a high molecular weight material may be given. In addition, it is often the case that an organic compound for a single layer or a laminate is generally used as a material that is used for an electroluminescent layer. However, the present invention includes a structure in which an inorganic compound is used for a part of a film comprising an organic compound.

In addition, as a material that is used for the second electrode (cathode) 417 formed on the electroluminescent layer 416, a material that has a small work function (Al, Ag, Li, or Ca, an alloy thereof such as MgAg, MgIn, AlLi, or $CaF_2$, or CaN) may be used. In the case of transmitting light generated in the electroluminescent layer 416 through the second electrode 417, it is preferable to use a laminate of a thinned metal and a transparent conductive film (such as ITO (an alloy of indium oxide and tin oxide), an alloy of indium oxide and zinc oxide ($In_2O_3$—ZnO), or zinc oxide (ZnO)) film as the second electrode (cathode) 417.

Further, a structure is obtained by bonding the sealing substrate 404 and the device substrate 410 with the sealing agent 405, where an electroluminescent device 418 is equipped in the space 407 surrounded by the device substrate 410, the sealing substrate 404, and the sealing agent 405. The space 407 also includes a composition of filling with the sealing agent 405 in addition to a case of filling with inert gas (such as nitrogen or argon).

It is preferable to use epoxy resin for the sealing agent 405. In addition, it is desirable that these materials are a material that allows no permeation of moisture or oxygen to as much as possible. Further, as a material that is used for the sealing substrate 404, a plastic substrate comprising FRP (Fiberglass-Reinforced Plastics), PVF (polyvinylfluoride), Mylar, polyester, acrylic, or the like can be used besides a glass substrate and a quarts substrate.

In this way, the light-emitting device that has the electroluminescent device according to the present invention can be obtained.

Embodiment 2

In the present embodiment, various electronic devices completed with the use of a light-emitting device that has an electroluminescent device according to the present invention will be described.

As electronic devices manufactured with the use of a light-emitting device that has an electroluminescent device according to the present invention, a video camera, a digital camera, a goggle-type display (head mount display), a navigation system, a sound reproduction device (such as an in-car audio system or an audio set), a laptop personal computer, a game machine, a personal digital assistance (such as a mobile computer, a mobile phone, a portable game machine, or an electronic book), an image reproduction device equipped with a recording medium (specifically, a device equipped with a display device that can reproduce a recording medium such as a digital versatile disc (DVD) and display the image), and the like can be given. FIGS. 5(A) to 5(G) show specific examples of these electronic devices.

Figure 5:
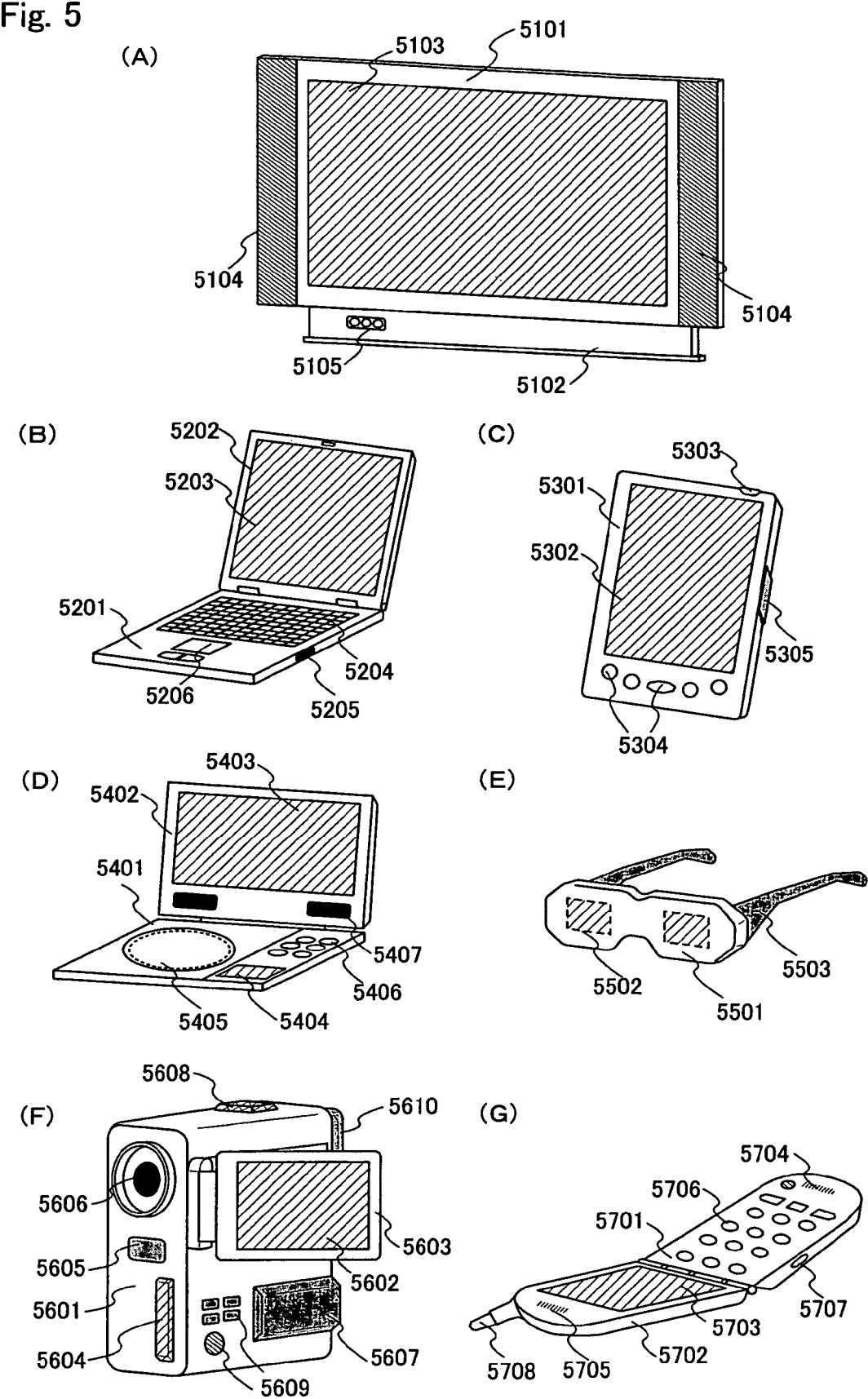
FIGS. 5(A) to 5(G) are diagrams describing electronic devices that use a light-emitting device according to the present invention.

FIG. 5(A) is a display device, which includes a frame body 5101, a support 5102, a display portion 5103, a speaker portion 5104, a video input terminal 5105, and the like. A light-emitting device that has an electroluminescent device according to the present invention is used for the display portion 2003. The display device includes all devices for displaying information such as for a personal computer, for receiving TV broad casting, and for displaying an advertisement.

FIG. 5(B) is a laptop personal computer, which includes a main body 5201, a frame body 5202, a display portion 5203, a keyboard 5204, an external connection port 5205, a pointing mouse 5206, and the like. A light-emitting device that has an electroluminescent device according to the present invention is used for the display portion 5203.

FIG. 5(C) is a mobile computer, which includes a main body 5301, a display portion 5302, a switch 5303, an operation key 5304, an infrared port 5305, and the like. A light-emitting device that has an electroluminescent device according to the present invention is used for the display portion 5302.

FIG. 5(D) is a portable image reproduction device equipped with a recording medium (specifically, a DVD reproduction device), which includes a main body 5401, a frame body 5402, a display portion A 5403, a display portion B 5404, a recording medium (such as DVD) reading portion 5405, an operation key 5406, a speaker portion 5407, and the like. The display portion A 5403 is used mainly for displaying image information while the display portion B 5404 is used mainly for displaying character information, and a light-emitting device that has an electroluminescent device according to the present invention is used for these display portion A 5403 and display portion B 5404. The image reproduction device equipped with the recording medium further includes a home game machine and the like.

FIG. 5(E) is a goggle-type display (head mount display), which includes a main body 5501, a display portion 5502, an arm portion 5503, and the like. A light-emitting device that has an electroluminescent device according to the present invention is used for the display portion 5502.

FIG. 5(F) is a video camera, which includes a main body 5601, a display portion 5602, a frame body 5603, an external connection port 5604, a remote control receiving portion 5605, an image receiving portion 5606, a battery 5607, a sound input portion 5608, an operation key 5609, an eye piece 5610, and the like. A light-emitting device that has an electroluminescent device according to the present invention is used for the display portion 5602.

FIG. 5(G) is a mobile phone, which includes a main body 5701, a frame body 5702, a display portion 5703, a voice input portion 5704, a voice output portion 5705, an operation key 5706, an external connection port 5707, an antenna 5708, and the like. A light-emitting device that has an electroluminescent device according to the present invention is used for the display portion 5703. The mobile phone can have power consumption suppressed by displaying white characters on a black background in the display portion 5703.

As described above, a light-emitting device that has an electroluminescent device according to the present invention is quite widely applied, and is applicable to electronic devices in all fields.

What is claimed is:

1. An organometallic complex represented by the following general formula 2,

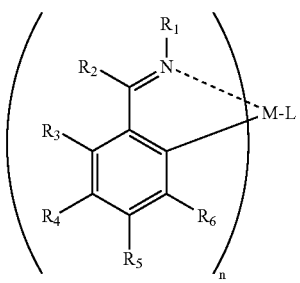

(Formula 2)

wherein $R_1$ is an alkyl group, an aryl group, a substituted aryl group, a heterocyclic group or a substituted heterocyclic group, wherein $R_2$ is an alkyl group, an aryl group, a substituted aryl group, a heterocyclic group, or a substituted heterocyclic group, wherein each of $R_3$, $R_4$, $R_5$, and $R_6$ is identical with each other or different from each other and is hydrogen, halogen, an alkyl group, an alkoxyl group, an aryl group, a substituted aryl group, a heterocyclic group, or a substituted heterocyclic group, wherein M is an element of Group 9 or an element of Group 10, wherein n is 2 when the M is the element of Group 9 or n is 1 when the M is the element of Group 10, and wherein L is any of monoanionic ligands shown by the following structure formulas 4 or 6:

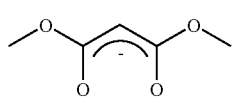

(Formula 4)

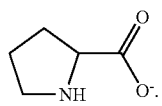

(Formula 6)

2. The organometallic complex according to claim 1, wherein the M is iridium or platinum.

3. A light emitting device comprising:
a first electrode over a substrate;
a light emitting layer comprising an organometallic complex represented by the following general formula 2, over the first electrode;
a second electrode over the light emitting layer,

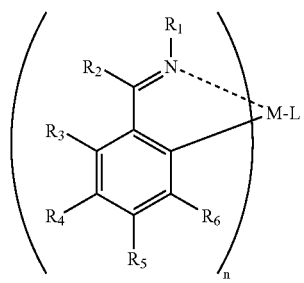

(Formula 2)

wherein $R_1$ is an alkyl group, an aryl group, a substituted aryl group, a heterocyclic group or a substituted heterocyclic group, wherein $R_2$ is an alkyl group, an aryl group, a substituted aryl group, a heterocyclic group, or a substituted heterocyclic group, wherein each of $R_3$, $R_4$, $R_5$, and $R_6$ is identical with each other or different from each other and is hydrogen, halogen, an alkyl group, an alkoxyl group, an aryl group, a substituted aryl group, a heterocyclic group, or a substituted heterocyclic group, wherein M is an element of Group 9 or an element of Group 10, wherein n is 2 when the M is the element of Group 9 or n is 1 when the M is the element of Group 10, and wherein L is any of monoanionic ligands shown by the following structure formulas 4 or 6:

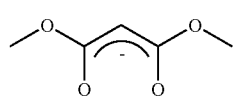

(Formula 4)

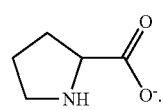

(Formula 6)

4. The light emitting device according to claim 3, wherein the M is iridium or platinum.

5. A light emitting device according to claim 3, wherein the light emitting device is incorporated into an electronic device selected from the group consisting of a video camera, a digital camera, a goggle-type display, a navigation system, a sound reproduction device, a laptop personal computer, a game machine, a mobile computer, a mobile phone, a portable game machine, an electronic book, and an image reproduction device.

6. A light emitting device according to claim 3, wherein a hole injection layer comprising a polymer material is formed adjacent to the light emitting layer.

7. A light emitting device according to claim 3, wherein a hole injection layer comprising a low molecular weight material is formed adjacent to the light emitting layer.

8. A light emitting device comprising:
a thin film transistor over a substrate;
an interlayer insulating film over the thin film transistor;
a first electrode electrically connected to the thin film transistor, over the interlayer insulating film;
a light emitting layer comprising an organometallic complex represented by the following general formula 2, over the first electrode;

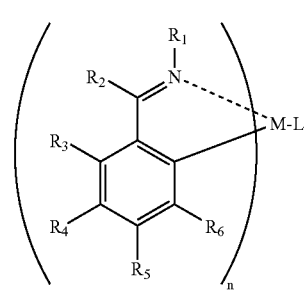

(Formula 2)

a second electrode over the light emitting layer,
wherein $R_1$ is an alkyl group, an aryl group, a substituted aryl group, a heterocyclic group or a substituted heterocyclic group,
wherein $R_2$ is an alkyl group, an aryl group, a substituted aryl group, a heterocyclic group, or a substituted heterocyclic group,
wherein each of $R_3$, $R_4$, $R_5$, and $R_6$ is identical with each other or different from each other and is hydrogen, halogen, an alkyl group, an alkoxyl group, an aryl group, a substituted aryl group, a heterocyclic group, or a substituted heterocyclic group,
wherein M is an element of Group 9 or an element of Group 10,
wherein n is 2 when the M is the element of Group 9 or n is 1 when the M is the element of Group 10, and
wherein L is any of monoanionic ligands shown by the following structure formulas 4 or 6:

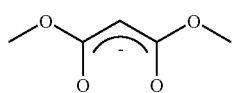

(Formula 4)

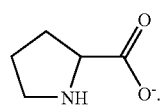

(Formula 6)

9. The light emitting device according to claim 8, wherein the M is iridium or platinum.

10. A light emitting device according to claim 8, wherein the light emitting device is incorporated into an electronic device selected from the group consisting of a video camera, a digital camera, a goggle-type display, a navigation system, a sound reproduction device, a laptop personal computer, a game machine, a mobile computer, a mobile phone, a portable game machine, an electronic book, and an image reproduction device.

11. A light emitting device according to claim 8, wherein a hole injection layer comprising a polymer material is formed adjacent to the light emitting layer.

12. A light emitting device according to claim 8, wherein a hole injection layer comprising a low molecular weight material is formed adjacent to the light emitting layer.

13. A light emitting device comprising:
a first electrode over a substrate;
a light emitting layer comprising an organometallic complex represented by the following general formula 2, over the first electrode;

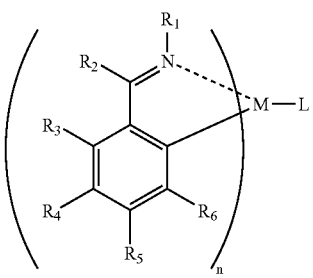

(Formula 2)

a second electrode over the light emitting layer,
wherein $R_1$ is an alkyl group, an aryl group, a substituted aryl group, a heterocyclic group or a substituted heterocyclic group,
wherein $R_2$ is an alkyl group, an aryl group, a substituted aryl group, a heterocyclic group, or a substituted heterocyclic group,
wherein each of $R_3$, $R_4$, $R_5$, and $R_6$ is identical with each other or different from each other, and is hydrogen, halogen, an alkyl group, an alkoxyl group, an aryl group, a substituted aryl group, a heterocyclic group, or a substituted heterocyclic group,
wherein M is an element of Group 10,
wherein n is 1, and
wherein L is a monoanionic ligand having a β-diketone structure, a monoanionic bidentate ligand having a carboxyl group, or a monoanionic bidentate ligand having a phenolic hydroxyl group.

14. The light emitting device according to claim 13, wherein the L is any of monoanionic ligands shown by the following structure formulas 3 to 9:

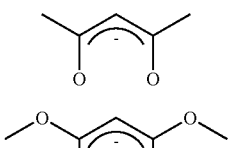

(Formula 3)

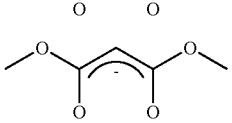

(Formula 4)

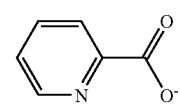

(Formula 5)

-continued (Formula 6)
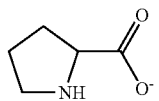

(Formula 7)
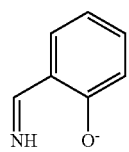

(Formula 8)
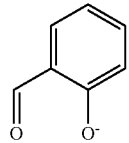

(Formula 9)
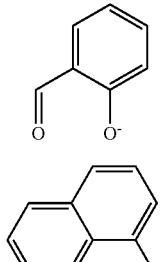

15. A light emitting device according to claim 13, wherein the light emitting device is incorporated into an electronic device selected from the group consisting of a video camera, a digital camera, a goggle-type display, a navigation system, a sound reproduction device, a laptop personal computer, a game machine, a mobile computer, a mobile phone, a portable game machine, an electronic book, and an image reproduction device.

16. A light emitting device according to claim 13, wherein a hole injection layer comprising a polymer material is formed adjacent to the light emitting layer.

17. A light emitting device according to claim 13, wherein a hole injection layer comprising a low molecular weight material is formed adjacent to the light emitting layer.

18. A light emitting device comprising:
a thin film transistor over a substrate;
an interlayer insulating film over the thin film transistor;
a first electrode electrically connected to the thin film transistor, over the interlayer insulating film;
a light emitting layer comprising an organometallic complex represented by the following general formula 2, over the first electrode;

(Formula 2)
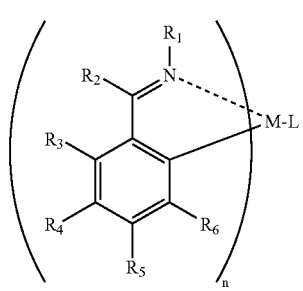

a second electrode over the light emitting layer,
wherein $R_1$ is an alkyl group, an aryl group, a substituted aryl group, a heterocyclic group or a substituted heterocyclic group, wherein $_2$ is an alkyl group, an aryl group, a substituted aryl group, a heterocyclic group, or a substituted heterocyclic group, wherein each of $_3$, $R_4$, $_5$, and $_6$ is identical with each other or different from each other, and is hydrogen, halogen, an alkyl group, an alkoxyl group, an aryl group, a substituted aryl group, a heterocyclic group, or a substituted heterocyclic group, wherein M is an element of Group 10, wherein n is 1, and wherein L is a monoanionic ligand having a β-diketone structure, a monoanionic bidentate ligand having a carboxyl group, or a monoanionic bidentate ligand having a phenolic hydroxyl group.

19. The light emitting device according to claim 18, wherein the L is any of monoanionic ligands shown by the following structure formulas 3 to 9:

(Formula 3)
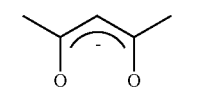

(Formula 4)
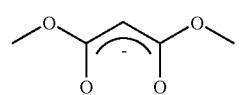

(Formula 5)
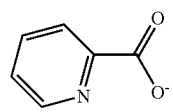

(Formula 6)
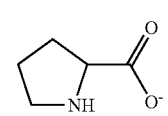

(Formula 7)

(Formula 8)
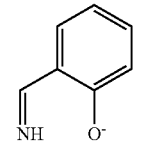

(Formula 9)
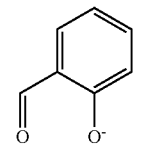

20. A light emitting device according to claim 18, wherein the light emitting device is incorporated into an electronic device selected from the group consisting of a video camera, a digital camera, a goggle-type display, a navigation system, a sound reproduction device, a laptop personal computer, a game machine, a mobile computer, a mobile phone, a portable game machine, an electronic book, and an image reproduction device.

21. A light emitting device according to claim 18, wherein a hole injection layer comprising a polymer material is formed adjacent to the light emitting layer.

22. A light emitting device according to claim 18, wherein a hole injection layer comprising a low molecular weight material is formed adjacent to the light emitting layer.

23. The organometallic complex according to claim 1, wherein the organometallic complex emits both fluorescence and phosphorescence.

24. The organometallic complex according to claim 23, wherein an emission from the organometallic complex is white or whitish lighting color.

25. The light emitting device according to claim 3, wherein the organometallic complex emits both fluorescence and phosphorescence.

26. The light emitting device according to claim 25, wherein an emission from the organometallic complex is white or whitish lighting color.

27. The light emitting device according to claim 8, wherein the organometallic complex emits both fluorescence and phosphorescence.

28. The light emitting device according to claim 27, wherein an emission from the organometallic complex is white or whitish lighting color.

29. The light emitting device according to claim 13, wherein the organometallic complex emits both fluorescence and phosphorescence.

30. The light emitting device according to claim 29, wherein an emission from the organometallic complex is white or whitish lighting color.

31. The light emitting device according to claim 18, wherein the organometallic complex emits both fluorescence and phosphorescence.

32. The light emitting device according to claim 31, wherein an emission from the organometallic complex is white or whitish lighting color.

33. The organometallic complex according to claim 1, wherein an excited spectrum of the organometallic complex has two peaks.

34. The light emitting device according to claim 3, wherein an excited spectrum of the organometallic complex has two peaks.

35. The light emitting device according to claim 8, wherein an excited spectrum of the organometallic complex has two peaks.

36. The light emitting device according to claim 13, wherein an excited spectrum of the organometallic complex has two peaks.

37. The light emitting device according to claim 18, wherein an excited spectrum of the organometallic complex has two peaks.

38. An organometallic complex represented by the following general formula 2,

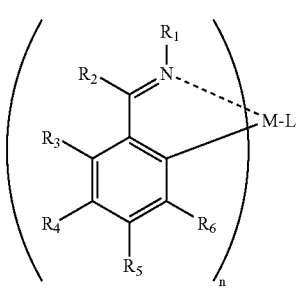

(Formula 2)

wherein $R_1$ is an alkyl group, an aryl group, a substituted aryl group, a heterocyclic group or a substituted heterocyclic group, wherein $R_2$ is an alkyl group, an aryl group, a substituted aryl group, a heterocyclic group, or a substituted heterocyclic group, wherein each of $R_3$, $R_4$, $R_5$, and $R_6$ is identical with each other or different from each other and is hydrogen, halogen, an alkyl group, an alkoxyl group, an aryl group, a substituted aryl group, a heterocyclic group, or a substituted heterocyclic group, wherein M is an element of Group 10, wherein n is 1, and wherein L is a monoanionic ligand having a β-diketone structure, a monoanionic bidentate ligand having a carboxyl group, or a monoanionic bidentate ligand having a phenolic hydroxyl group.

39. The organometallic complex according to claim 38, wherein the M is platinum.

40. The organometallic complex according to claim 38, wherein the L is any of monoanionic ligands shown by the following structure formulas 3 to 9:

(Formula 3)

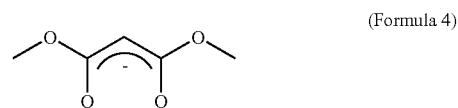

(Formula 4)

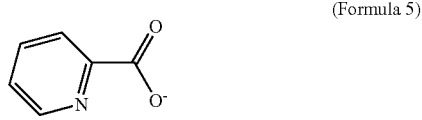

(Formula 5)

(Formula 6)

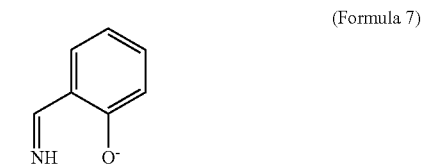

(Formula 7)

(Formula 8)

(Formula 9)

41. The organometallic complex according to claim 38, wherein the organometallic complex emits both fluorescence and phosphorescence.

42. The organometallic complex according to claim 38, wherein an emission from the organometallic complex is white or whitish lighting color.

43. The organometallic complex according to claim 38, wherein an excited spectrum of the organometallic complex has two peaks.

* * * * *